United States Patent [19]

Nakamura et al.

[11] Patent Number: 5,627,583

[45] Date of Patent: May 6, 1997

[54] ELECTROENDOSCOPE APPARATUS

[75] Inventors: Kazunari Nakamura, Hino; Hisao Yabe, Hachioji; Shigeru Nakajima, Hachioji; Hiroyuki Sasa, Hachioji; Katsuyuki Saito, Hachioji; Yoshihiro Okada, Hachioji; Seiji Yamaguchi, Hachioji, all of Japan

[73] Assignee: Olympus Optical Co., Ltd., Tokyo, Japan

[21] Appl. No.: 261,249

[22] Filed: Jun. 14, 1994

Related U.S. Application Data

[63] Continuation of Ser. No. 980,751, Nov. 24, 1992, abandoned.

[30] Foreign Application Priority Data

Feb. 7, 1992 [JP] Japan .................................. 4-022896
Aug. 26, 1992 [JP] Japan .................................. 4-227559

[51] Int. Cl.$^6$ .................................. A61B 1/05; H04N 7/18
[52] U.S. Cl. .................................. 348/72; 348/65
[58] Field of Search .................................. 348/65, 77, 68, 348/69, 72, 70, 74, 75; H04N 7/18; A61B 1/05

[56] References Cited

U.S. PATENT DOCUMENTS

| | | | |
|---|---|---|---|
| 4,816,909 | 3/1989 | Kimura et al. | 348/65 |
| 4,878,112 | 10/1989 | Ieoka | 348/70 |
| 4,891,695 | 1/1990 | Uchikubo et al. | 348/65 |
| 4,926,258 | 5/1990 | Sasaki et al. | 358/98 |
| 4,983,019 | 1/1991 | Ikuno et al. | 350/313 |
| 5,162,913 | 11/1992 | Chatenever et al. | 348/65 |

FOREIGN PATENT DOCUMENTS 63-186618  8/1988  Japan .
1-297044  11/1989  Japan .

OTHER PUBLICATIONS

Xilinx–XC4000 Logic Cell Array Family Programmable Gate Arrays, 1990.
Programmable Gate Arrays, Technical Data, XC 4000, Logic Cell Array Family, 1990, Xilinx, Inc.

*Primary Examiner*—Thai Q. Tran
*Assistant Examiner*—Vu Le
*Attorney, Agent, or Firm*—Armstrong, Westerman, Hattori, McLeland & Naughton

[57] ABSTRACT

An electroendoscope apparatus which uses a plurality of types of electroendoscopes having solid-state imaging devices of different specifications and which performs signal processing on the basis of a plurality of signal processing systems, which includes: a video memory device used commonly among the plurality of signal processing systems; a circuit data recording device for recording circuit data corresponding to each of the plurality of signal processing systems; and a signal processing device, composed of programmable logic elements, which forms a dedicated processing circuit corresponding to each of the plurality of signal processing systems on the basis of the circuit data recorded by the circuit data recording device.

11 Claims, 10 Drawing Sheets

ELECTROENDOSCOPE APPARATUS

This application is a continuation of application Ser. No. 07/980,751 filed Nov. 24, 1992, now abandoned.

BACKGROUND OF THE INVENTION

1. Field of the Invention

The present invention relates to an electroendoscope apparatus to which a plurality of types of endoscopes having different types of solid-state imaging devices are connected.

2. Description of the Related Art

As is well known, an electroendoscope apparatus makes it possible to observe the inside of living bodies or the like which cannot be observed directly by the naked eye and is widely used for observation and curing mainly in the field of medical treatment. In recent years, electroendoscope apparatuses which convert a subject image into electrical signals by using solid-state imaging devices, such as CCDs, so as to enable the image to be observed by a monitor, have come to be widely used.

Various types of endoscopes corresponding to the places to be observed by the electroendoscope apparatus are used. These endoscopes are connected to a light source apparatus, a signal processing apparatus or the like and then used. Therefore, a plurality of types of signal processing circuits are needed to handle the types of solid-state imaging devices provided in the endoscope.

Accordingly, for the purpose of providing an apparatus which can operate a plurality of types of endoscopes having solid-state imaging devices each having a different number of pixels, an apparatus having a detection circuit of an endoscope is provided in the main body thereof has been disclosed in Japanese Patent Laid-Open No. 63-186618. This apparatus switches to the most appropriate endoscope according to the detected signals, depending upon the endoscopes to which drive pulses for the solid-state imaging device and a signal processing circuit are connected.

In addition, an electroendoscope apparatus has been disclosed in U.S. Pat. No. 4,891,695, in which features in the arrangement of pixels, such as pixel size, are made the same in two or more solid-state imaging devices of a plurality of the usable solid-state imaging devices within the apparatus. This apparatus is designed to easily switch a signal processing circuit corresponding to an endoscope having different solid-state imaging devices by using a low-cost arrangement.

However, since dedicated circuits corresponding to each of the solid-state imaging devices must be provided and switched in the conventional electroendoscope apparatus, its circuitry becomes complex and the apparatus becomes enlarged. When an endoscope having solid-state imaging devices having pixel arrangements which are quite different is used, signal processing apparatuses having different constructions need to be switched. Thus, the apparatus also becomes complex.

SUMMARY OF THE INVENTION

A first object of the present invention is to provide an electroendoscope apparatus which is usable for a plurality of different types of endoscopes or endoscopes of a plurality of systems, in which common circuits are used without providing a plurality of types of solid-state imaging devices, or dedicated circuits usable for a plurality of imaging systems or TV systems. Thus, the scale of the circuits is reduced.

A second object of the present invention is to provide an electroendoscope apparatus which is capable of performing signal processing most suitable for electroendoscopes used without requiring dedicated circuits for each solid-state imaging device, so as to make it possible to process signals from a plurality of types of solid-state imaging devices.

A third object of the present invention is to provide an electroendoscope apparatus which does not require individual dedicated circuits in a plurality of types of endoscopes having different solid-state imaging devices or endoscopes of a plurality of systems and which is capable of configuring system flexibly.

A fourth object of the present invention is to provide an electroendoscope apparatus having a small amount of circuitry which is usable for a plurality of systems irrespective of differences in the number of pixels of solid-state imaging devices, and differences in TV systems, imaging systems or the like.

To these ends, according to the present invention, there is provided an electroendoscope apparatus which uses a plurality of types of electroendoscopes having solid-state imaging devices of different specifications and which performs signal processing in conformity with a plurality of signal processing systems, the electroendoscope apparatus comprising: video memory means used commonly among the plurality of signal processing systems; circuit data recording means for recording circuit data corresponding to the plurality of signal processing systems; and signal processing means, composed of programmable logic elements, which forms dedicated processing circuits corresponding to each of the plurality of signal processing systems on the basis of circuit data recorded by the circuit data recording means.

The above and further objects and novel features of the invention will more fully appear from the following detailed description when the same is read in connection with the accompanying drawings. It is to be expressly understood, however, that the drawings are for the purpose of illustration only and are not intended as a definition of the limits of the invention.

BRIEF DESCRIPTION OF THE DRAWINGS

FIGS. 1(a) and 1(b) are views schematically illustrating the construction of an electroendoscope apparatus according to a first embodiment of the present invention, in which FIG. 1(a) illustrates the construction of the electroendoscope apparatus when an endoscope having a high-density pixel type solid-state imaging device is connected to the electroendoscope apparatus, and FIG. 1(b) illustrates the construction of the apparatus when an endoscope having a compact solid-state imaging device is connected to the electroendoscope apparatus;

DETAILED DESCRIPTION OF THE PREFERRED EMBODIMENTS

The first embodiment of the present invention will be explained below with reference to FIGS. 1 to 5.

Figure 1A:
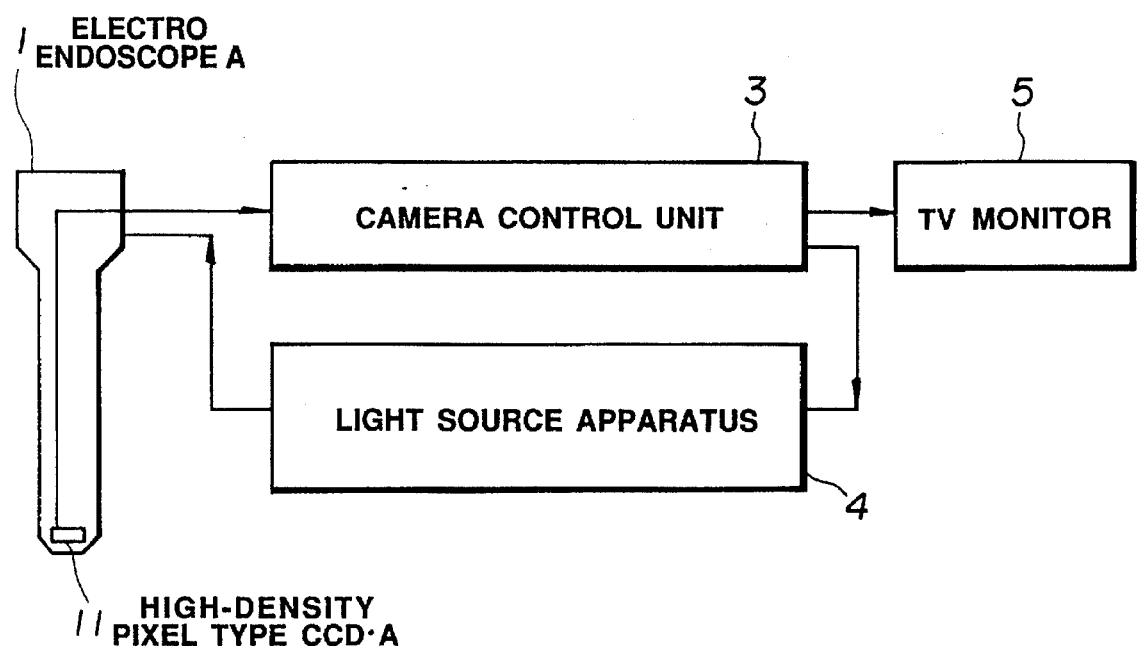
Figure 1B:
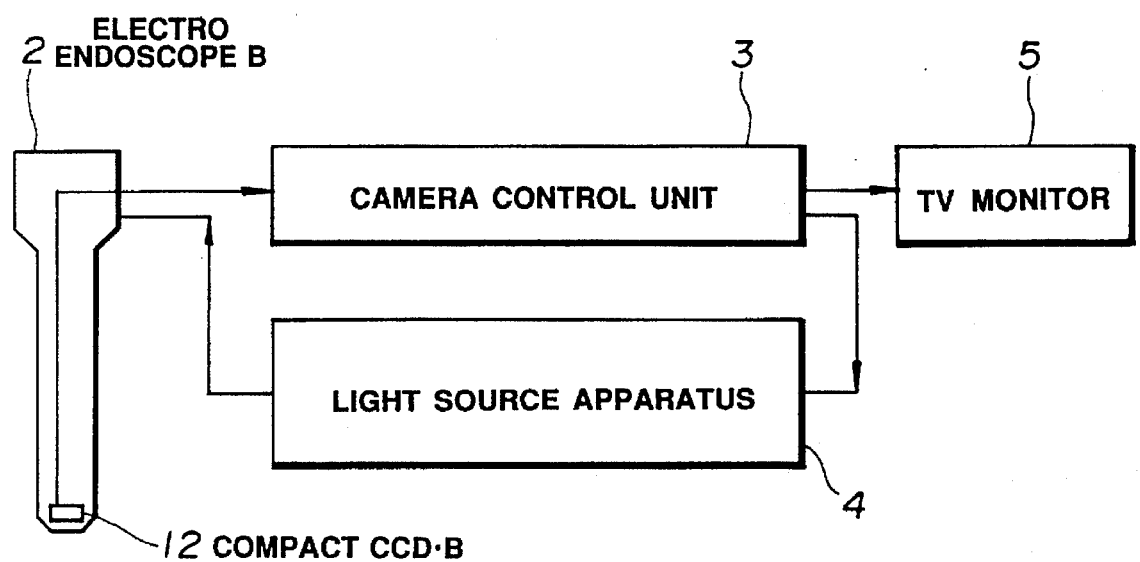

As shown in FIG. 1(a), an electroendoscope A1 is provided with a high-density type CCD.A11 having many pixels serving as a solid-state imaging device in the extreme end portion thereof in order that it can easily detect very small physical changes caused by a disease even though the outer dimensions of the electroendoscope are large. As shown in FIG. 1(b), an electroendoscope B2 is provided with a compact CCD.B12 having a small number of pixels as a solid-state imaging device in an extreme end portion thereof and is suitable for observing narrow lumina, such as bronchi, because the outer dimensions of the electroendoscope are small though the resolution thereof is slightly lower than that of the electroendoscope A1. An electroendoscope apparatus of this embodiment is so arranged that the electroendoscope A1 and the electroendoscope B2 can be connected to each other.

The electroendoscopes A1 and B2 are connected to a camera control unit 3 which controls the electroendoscopes A1 and B2 whose arrangements of CCDs are different from each other and which outputs video signals suitable for observation even with different types of CCDs. The camera control unit is also connected to a light source apparatus 4 which generates illumination light used for observation. A TV monitor 5 which inputs video signals for observation and displays a subject image is connected to the camera control unit 3 so that the subject image obtained by the electroendoscope A1 or B2 can be displayed on the TV monitor 5.

Figure 2:
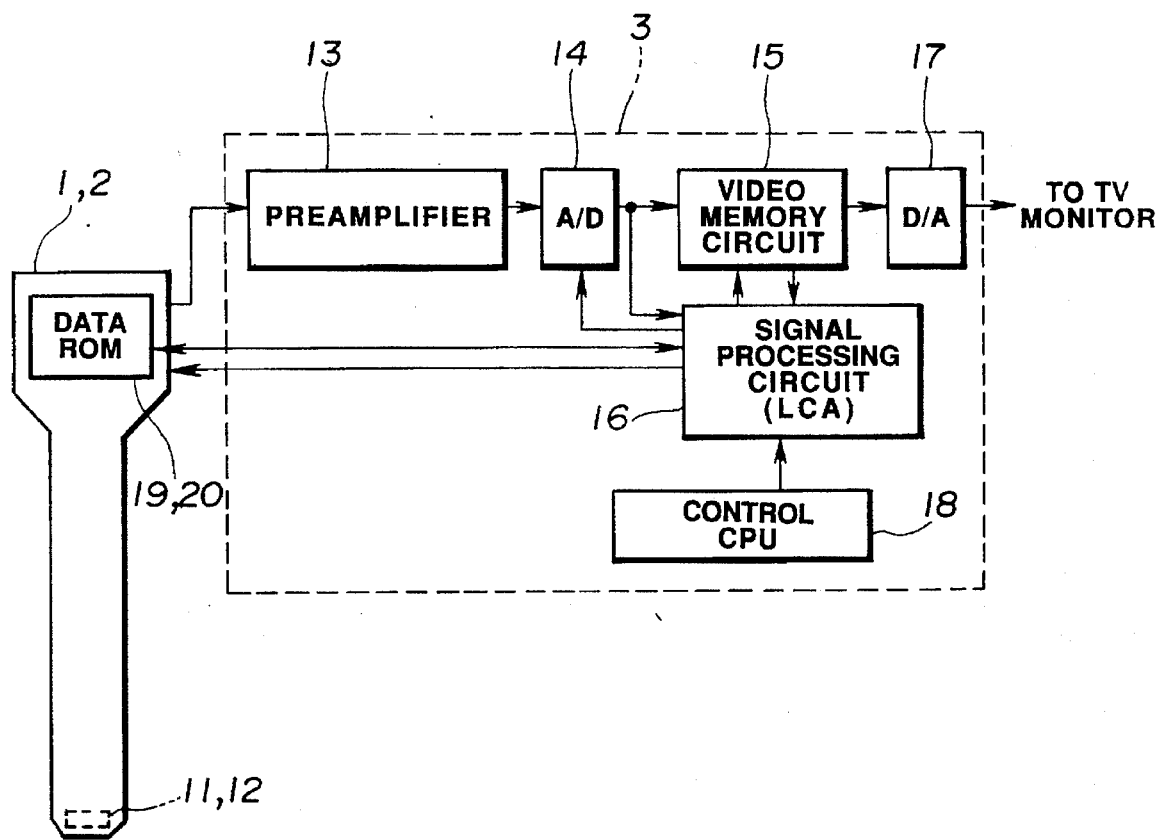
FIG. 2 is a block diagram illustrating the construction of the electroendoscope apparatus according to the first embodiment.

The construction of the camera control unit 3 is shown in FIG. 2. The camera control unit 3 is provided with a preamplifier 13 for amplifying output signals from the CCD.A11 and CCD.B12 of the electroendoscopes A1 and B2, respectively. The preamplifier 13 is connected to an A/D converter 14 for converting amplified image signals into digital signals. The A/D converter 14 is connected to a video memory circuit 15 which serves as video memory means for storing signals output from the A/D converter 14 and to a signal processing circuit 16 which serves as signal processing means for controlling the video memory circuit 15 and processing image data from the video memory circuit 15 and image signals from the A/D converter 14. Signal processing is performed so as to obtain video signals which can be displayed on the TV monitor 5.

The signal processing circuit 16 is formed of a logic cell array (LCA), which is one type of a field programmable gate array (FPGA), so that it can be programmed on the basis of circuit data. The input of the D/A converter 17 is connected to the output of the video memory circuit 15. Digital video signals stored in the video memory circuit 15 when signal processing is performed by the signal processing circuit 16 are converted by the D/A converter 17 into analog signals and output to the TV monitor 5.

Various types of peripheral units and a CPU 18 for controlling a front operation panel are also provided in the camera control unit 3. The peripheral units and the CPU 18 are connected to the signal processing circuit 16.

Data ROMs 19 and 20, which serve as circuit data recording means in which circuit data corresponding to respective built-in CCDs are recorded, are provided within the electroendoscopes A1 and B2, respectively.

Figure 3:
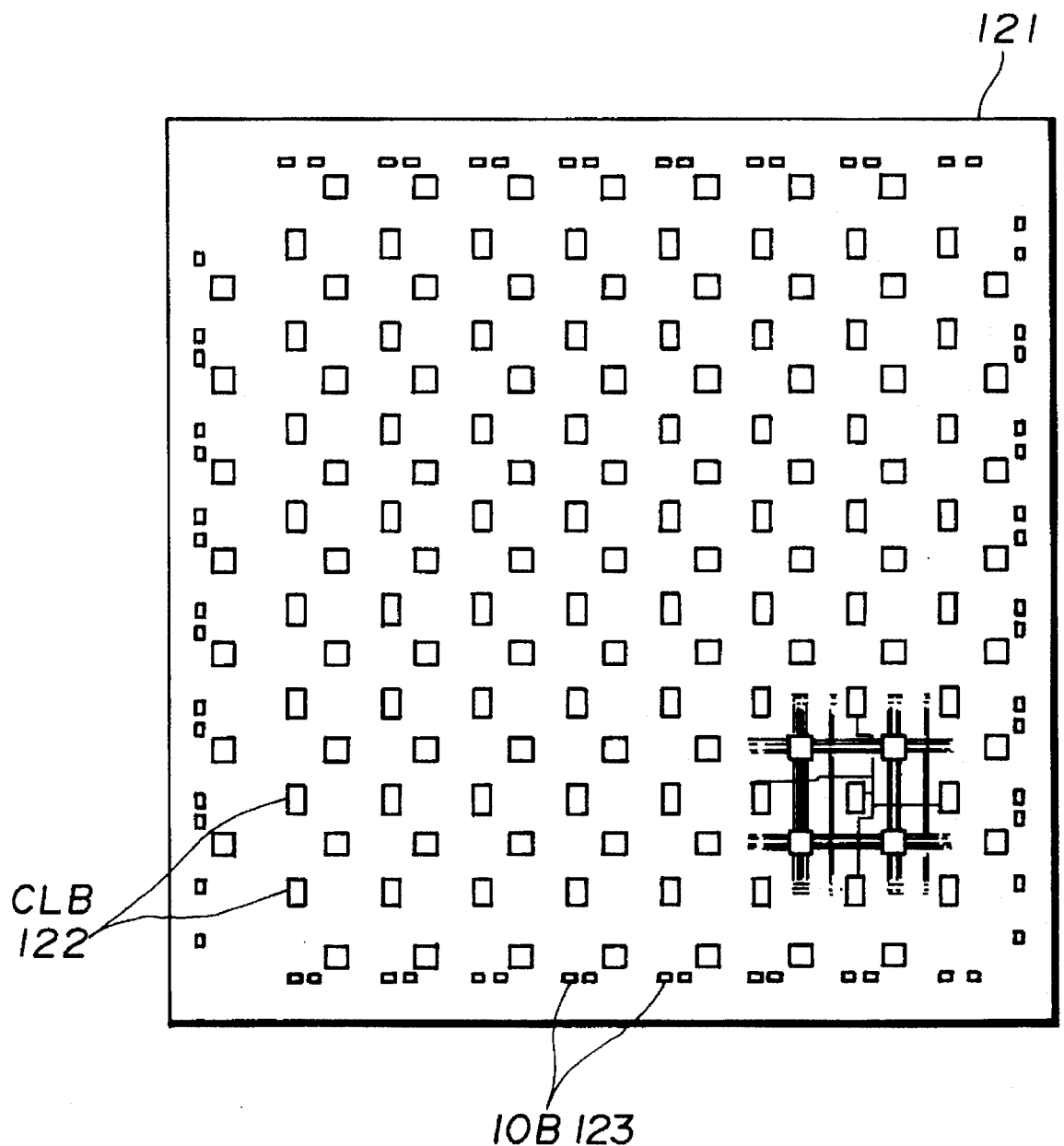
FIG. 3 is a view schematically illustrating the construction of a logic cell array (LCA) according to the first embodiment.

As shown in FIG. 3, an LCA 121 is a logic IC driven by a program in the same manner as a microcomputer. A matrix of logic blocks (configurable logic block: CLB) 122 is provided inside the LCA 121, and a plurality of I/O blocks (IOB) 123 are arranged in the peripheral portion of the logic blocks 122. The functions of these logic blocks 122 and I/O blocks 123, and the internal connection thereof may be configured. A logic circuit is formed by a configuration program based on the circuit data mentioned above.

The I/O blocks 123 can be programmed so that each block becomes a port for either input, output, or both. Data is transmitted from the I/O blocks 123 to the logic blocks 122 and vice versa. The logic blocks 122 have programmable combination circuits and storage registers so that a logic circuit is formed on the basis of input data. Programmable switches (not shown) are arranged in a matrix form in the LCA 121 so that the internal connection of arbitrary points on the chip may be formed by a program. Logic blocks 122 are connected to I/O blocks 123 as desired by turning on or off the switching matrix on the basis of the circuit data.

Next, the operation of this embodiment will be explained.

As previously mentioned in FIG. 2, data ROMs 19 and 20, in which the circuit data of the signal processing circuit 16 is recorded, are provided within the electroendoscopes A1 and B2, respectively. The camera control unit 3 usable for a plurality of types of CCDs is formed by changing the circuit of the signal processing circuit 16 formed of an LCA on the basis of the circuit data so that the CCD can be used for each of the electroendoscopes.

When the electroendoscope A1 is connected to the camera control unit 3, circuit data is loaded from data ROM 19 into the signal processing circuit 16. Thereupon, the signal processing circuit 16 forms a processing circuit for performing optimum processing on each of the connected electroendoscopes.

Then, a signal for driving CCD.A11 is input from the signal processing circuit 16 to the electroendoscope A1. Image signals obtained by the CCD.A11 are amplified by the preamplifier 13. The amplified image signals are converted into digital signals by the A/D converter 14 and stored in the video memory circuit 15. The image signals are also converted into standard TV signals by the signal processing circuit 16. The video signals converted into standard TV signals are converted into analog signals by the D/A converter 17 and output to the TV monitor 5.

The CPU 18 for control purposes inputs control signals from an unillustrated front operation panel, performs communication with the light source apparatus 4, and controls various peripheral units on the basis of input control signals or the like.

Figure 4:
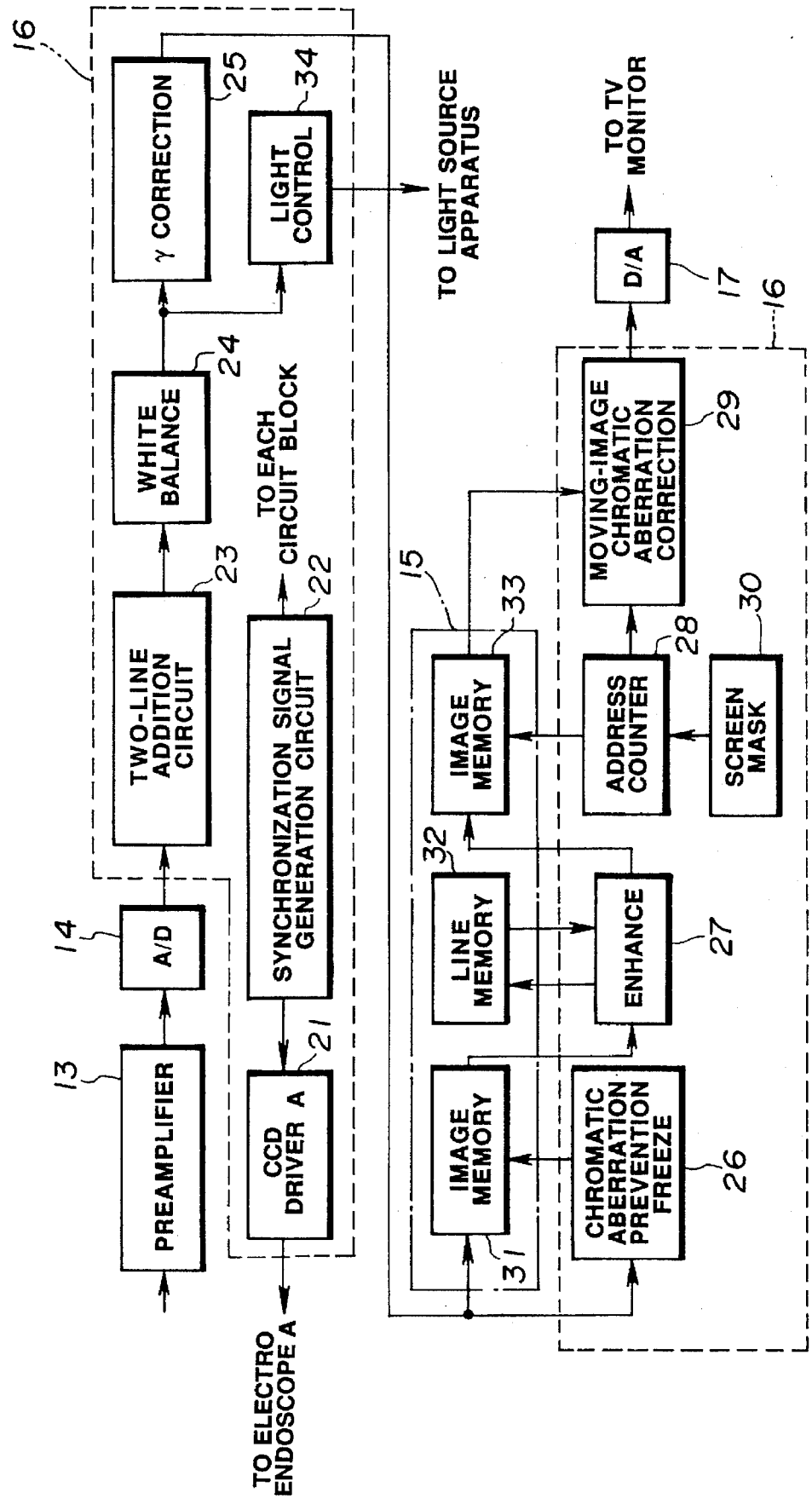
FIG. 4 is a block diagram illustrating the functional arrangement of a signal processing circuit in a case where a high-density pixel type solid-state imaging device is connected to the electroendoscope according to the first embodiment.

Referring now to FIG. 4, the operation of the video memory circuit 15 and the signal processing circuit 16 will be explained in detail.

The portions surrounded by dashed lines indicate function blocks of the signal processing circuit 16 based on an LCA formed of circuit data from the data ROM 19. The portion surrounded by an alternately long and short dashed line indicates a function block of the video memory circuit 15.

The high-density type CCD.A11 provided in the electroendoscope A1 is driven by signals generated by a CCD driver A21. System clock outputted to each synchronization circuit and timing signals required for each circuit are generated by a synchronization signal generation circuit 22 and output to each circuit.

On the other hand, signals of the image obtained by the CCD.A11 are input to a two-line addition circuit 23 through the preamplifier 13 and the A/D converter 14. Video signals which are read out simultaneously from two lines are added by the two-line addition circuit 23. The reason for reading out signals simultaneously from two lines is to read out all data within a period of one field because the CCD.A11 provided in the electroendoscope A1 is of a high-density type and the number of pixels is large. In this way, regular video signals are obtained by adding signals from two lines.

Then, the levels of the image signals of R, G and B of the signals added by the two-line addition circuit 23 are made to meet with each other by a white balance circuit 24. At this time, the levels of the image signals of R, G and B are held digitally, and the gain is adjusted so that the levels of the RGB signals become equal. The gradations of white balanced video signals converted by a γ correction circuit 25 are converted so that when the video signals are displayed on the TV monitor 5, correct gradation characteristics are shown.

The γ-corrected video signals are stored in an image memory 31 and also input to a chromatic aberration prevention freeze circuit 26. The chromatic aberration prevention freeze circuit 26 performs freezing by a combination of RGB which produces the smallest amount of chromatic aberration of RGB in a fixed amount of period. In this case, the correlation of RGB is detected, and the image memory 31 is controlled so that video signals recorded in the image memory are output by a combination of RGB having the highest correlation.

Vertical and horizontal highlighting operations are performed on the video signals output from the image memory 31 by an enhance circuit 27. The video signals are stored in a line memory 32 and used when this highlighting operation is performed. Therefore, the enhance circuit 27 also controls the line memory 32.

The video signals in which improvements are made in their wide areas by the enhance circuit 27 are stored in an image memory 33. Correction of chromatic aberrations during observation is performed by an address counter 28 and an moving-image chromatic aberration correction circuit 29. In this correction, data is stored in the image memory 33 in a period during which the color signals of R, G and B change, and pixels which have changed are detected by comparing the stored data with the current data. Pixels which are determined to have chromatic aberrations from among the pixels which have changed are corrected by the moving-image chromatic aberration correction circuit 29.

The image memory 33 in which RGB signals are recorded is controlled by the address counter 28.

A screen mask signal generation circuit 30 generates a mask signal for masking areas other than the image pick-up areas of the CCD of the area displayed on the TV monitor 5, and inputs the mask signal to the address counter 28 so that the area in which the address counter 28 should be updated is determined by the screen mask signal. The video signals in which chromatic aberrations during the observation of the moving image has been corrected by the moving-image chromatic aberration correction circuit 29 are converted into analog signals by the D/A converter 17 and output to the TV monitor 5.

The video signals white-balanced by the white balance circuit 24 are input to a light-control circuit 34 in which a signal for controlling the aperture of the light source apparatus 4 is generated on the basis of the video signals.

Next, a detailed explanation will be given about the operation of the video memory circuit 15 and the signal processing circuit 16 in the case where the compact electroendoscope B2 is connected to the camera control unit 3.

Figure 5:
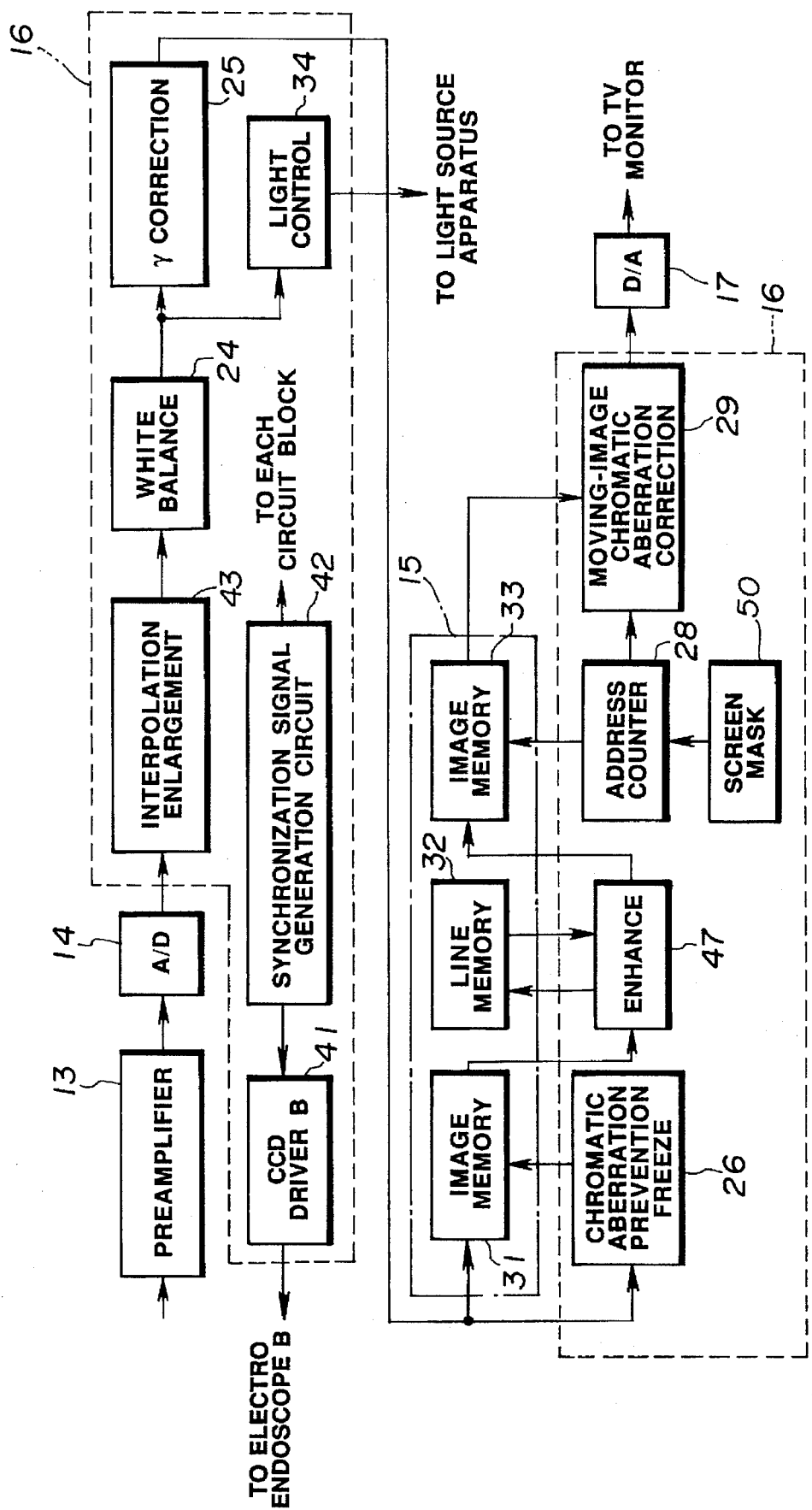
FIG. 5 is a block diagram illustrating the functional arrangement of the signal processing circuit in a case where a compact solid-state imaging device is connected to the electroendoscope according to the first embodiment.

When the electroendoscope B2 is connected to the camera control unit 3, circuit data is loaded into the signal processing circuit 16 from data ROM 20 provided within the electroendoscope B2 in the same manner as in the electroendoscope A1. Thereupon, the function block shown in FIG. 5 is formed in the signal processing circuit 16. The same components as when the electroendoscope A1 is connected are given the same reference numerals, and only portions which differ will be explained.

Image signals amplified by the preamplifier 13 and converted into digital signals by the A/D converter 14 have a small number of pixels. Since an observed image is displayed on only a part of the screen unless otherwise modified, vertical and horizontal interpolation operations are performed by an interpolation and enlargement circuit 43. Since enhancement corresponding to the number of effective pixels is performed by an enhance circuit 47, it enhances video signals whose frequencies are slightly lower than those in the electroendoscope A1. Therefore, the setting of the enhance circuit 47 is different from that of the enhance circuit 27 used in the electroendoscope A1.

Although the display area for the image on the TV monitor is enlarged by the interpolation and enlargement circuit 43 to a display area substantially the same as in the high-density pixel type electroendoscope A1, the display area is slightly different. Therefore, a screen mask signal generation circuit 50 for outputting mask signals is also changed. Furthermore, unlike the electroendoscope A1, simultaneous reading from two lines need not to be performed by a CCD driver.B41. However, since reading at the most appropriate frequency is required, a dedicated drive circuit is formed in the CCD driver.B41. Also, since the system clock required for each synchronization circuit is different, a synchronization signal generation circuit 42 is adapted for the electroendoscope B2.

According to this embodiment, as described above, circuit data for a signal processing circuit required for each CCD is provided within the electroendoscope, and a signal processing circuit corresponding to a connected electroendoscope is formed on the basis of the circuit data. As a result, unlike the prior art, a dedicated circuit for each CCD need not to be provided beforehand within the camera control unit to make it possible to process signals from a plurality of CCDs, and signal processing most appropriate for the electroendoscope used can be performed. Thus, one circuit can be used commonly and the scale of the circuit can be reduced.

In addition, a video memory can be used commonly. The case where three or more different CCDs will be used in the future can be handled, and a new camera control unit need not to be added. As a result, an endoscope system can be constructed flexibly, reducing the cost of the system as a whole.

Figure 6:
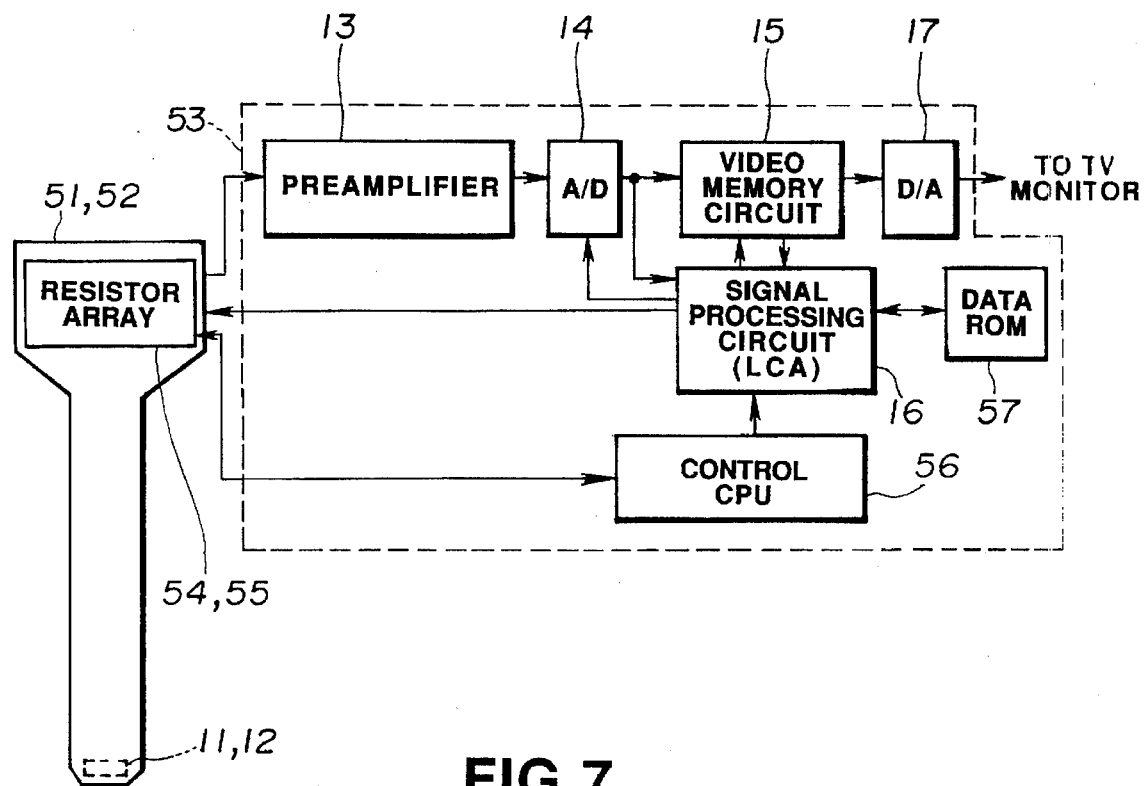
FIG. 6 is a block diagram illustrating the construction of an electroendoscope apparatus according to a second embodiment of the present invention.

The second embodiment of the present invention will be explained below with reference to FIG. 6.

The second embodiment concerns an example in which data ROM for recording circuit data beforehand is provided within a camera control unit, and the method of loading circuit data is changed.

An electroendoscope A51 having the high-resolution type CCD.A11, or an electroendoscope B52 having the compact CCD.B12, is connected to a camera control unit 53. A subject image obtained by the electroendoscope and whose signals are processed by the camera control unit 53 is displayed on the TV monitor 5. Components which are the same as in the first embodiment are given the same reference numerals, and thus an explanation thereof is omitted.

Resistor arrays 54 and 55 are provided within the electroendoscopes A51 and B52, respectively, to make it possible to identify the type of the endoscopes. A control CPU 56 for identifying the type of electroendoscopes, and a data ROM for prerecording circuit data corresponding to the type of the endoscope are provided within the camera control unit 53. When the electroendoscopes A51 and B52 are connected to the camera control unit 53, the control CPU 56 identifies the type of the electroendoscope (the type of the CCD) by resistor arrays 54 and 55 provided within the electroendoscopes. Namely, the resistor arrays 54 and 55, and the control CPU 56 constitute endoscope type identifying means.

Based on the identified results, circuit data corresponding to the type of endoscope is loaded from a data ROM 57 within the camera control unit 53 to the signal processing circuit 16 formed of a programmable FPGA, and an optimum processing circuit is formed for each of electroendoscopes connected in the same manner as in the first embodiment. As a result, image signals obtained by the CCDs.A11 and B12 are subjected to signal processing for each CCD, and displayed on the TV monitor 5.

According to this embodiment, as described above, large-scale circuit data is provided within the camera control unit beforehand and a signal processing circuit is formed on the basis of that data. Therefore, circuit data need not to be contained in each electroendoscope, and the electroendoscope can be formed at a low cost.

The other operations and advantages of this embodiment are the same as in the first embodiment.

Figure 7:
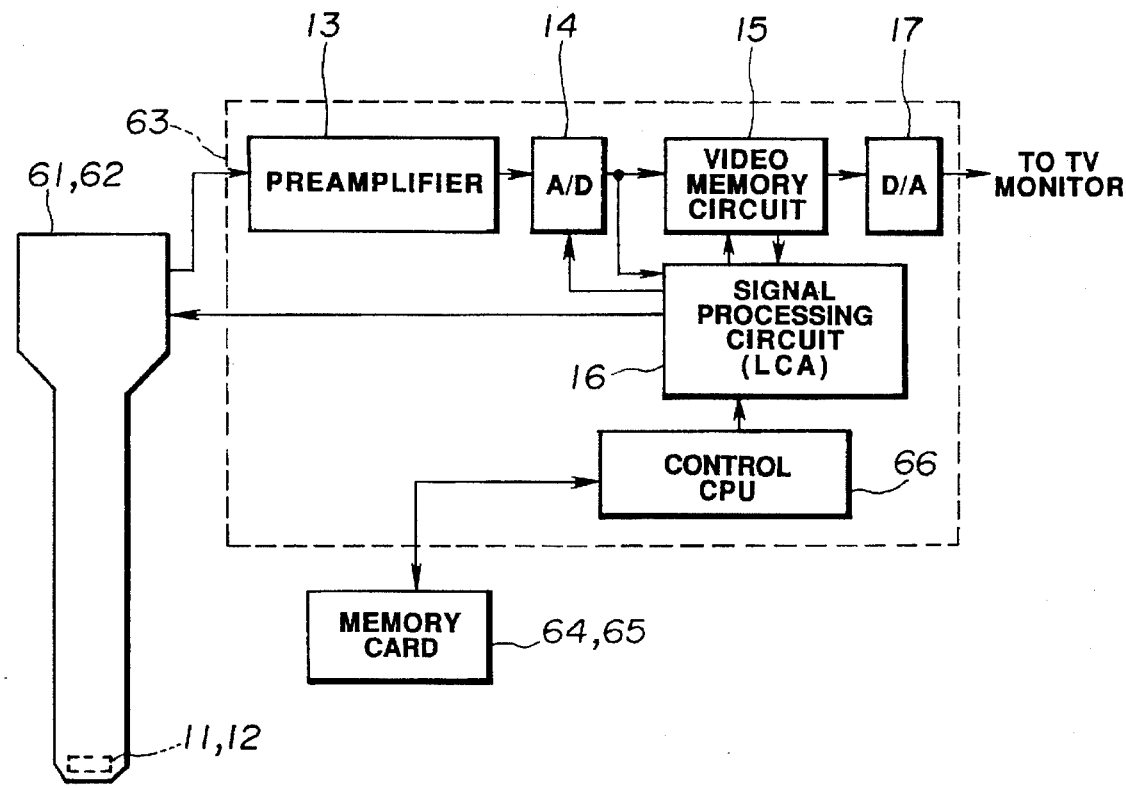
FIG. 7 is a block diagram illustrating the construction of an electroendoscope apparatus according to a third embodiment of the present invention.

The third embodiment of the present invention will be explained below with reference to the block diagram in FIG. 7.

Data ROM in which circuit data is prerecorded is not provided within electroendoscopes A61 and B62 or a camera control unit 63. Circuit data is loaded to the signal processing circuit 16 via a control CPU 66 by using memory cards 64 and 65 in which circuit data for each of the electroendoscope are prerecorded so that a processing circuit corresponding to each endoscope is formed. Components which are the same as in the first embodiment are given the same reference numerals, and thus an explanation thereof is omitted.

After the electroendoscopes A61 and B62 are connected to the camera control unit 63, the memory cards 64 and 65 are inserted into an unillustrated memory slot or the like of the camera control unit 63. The circuit data recorded in the memory cards 64 and 65 is loaded to the signal processing circuit 16 via the CPU 66. Thus, an optimum processing circuit corresponding to the type of the electroendoscope connected is formed in the same manner as in the first embodiment. As a result, image signals obtained by the CCD.A11 and CCD.B12 are subjected to the signal processing most appropriate for each CCD, and displayed on the TV monitor 5.

According to this embodiment, as described above, since circuit data is not provided within each electroendoscope or a camera control unit, an electroendoscope can be formed into a compact unit at low cost. Also, since various types of extended functions can be supplied in the form of memory cards, various types of extended functions can be added after the electroendoscope is purchased, thereby increasing the system's flexibility.

The other operations and advantages of this embodiment are the same as in the first embodiment. The signal processing circuit may be formed so as to operate not only for a plurality of types of CCDs as in the above-described first embodiment, but also for a plurality of TV systems, such as NTSC or PAL system.

Also, in order to operate for electroendoscopes whose imaging methods are different, as in the surface sequential system endoscope and a simultaneous system endoscope, video memories required for both systems, and a control CPU are not changed for the imaging system of the endoscope. A signal processing circuit may be formed of a field programmable gate array (FPGA) (an LCA is one type of FPGA).

The embodiment constructed in the above-described way will be explained below.

The fourth embodiment of the present invention will be explained below with reference to FIGS. 8 to 12.

A camera control unit 70 of this embodiment is capable of operating in both NTSC and PAL TV systems, as well as in imaging systems based on simultaneous systems and surface sequential systems, and capable of operating for a plurality of types of CCDs.

Figure 8:
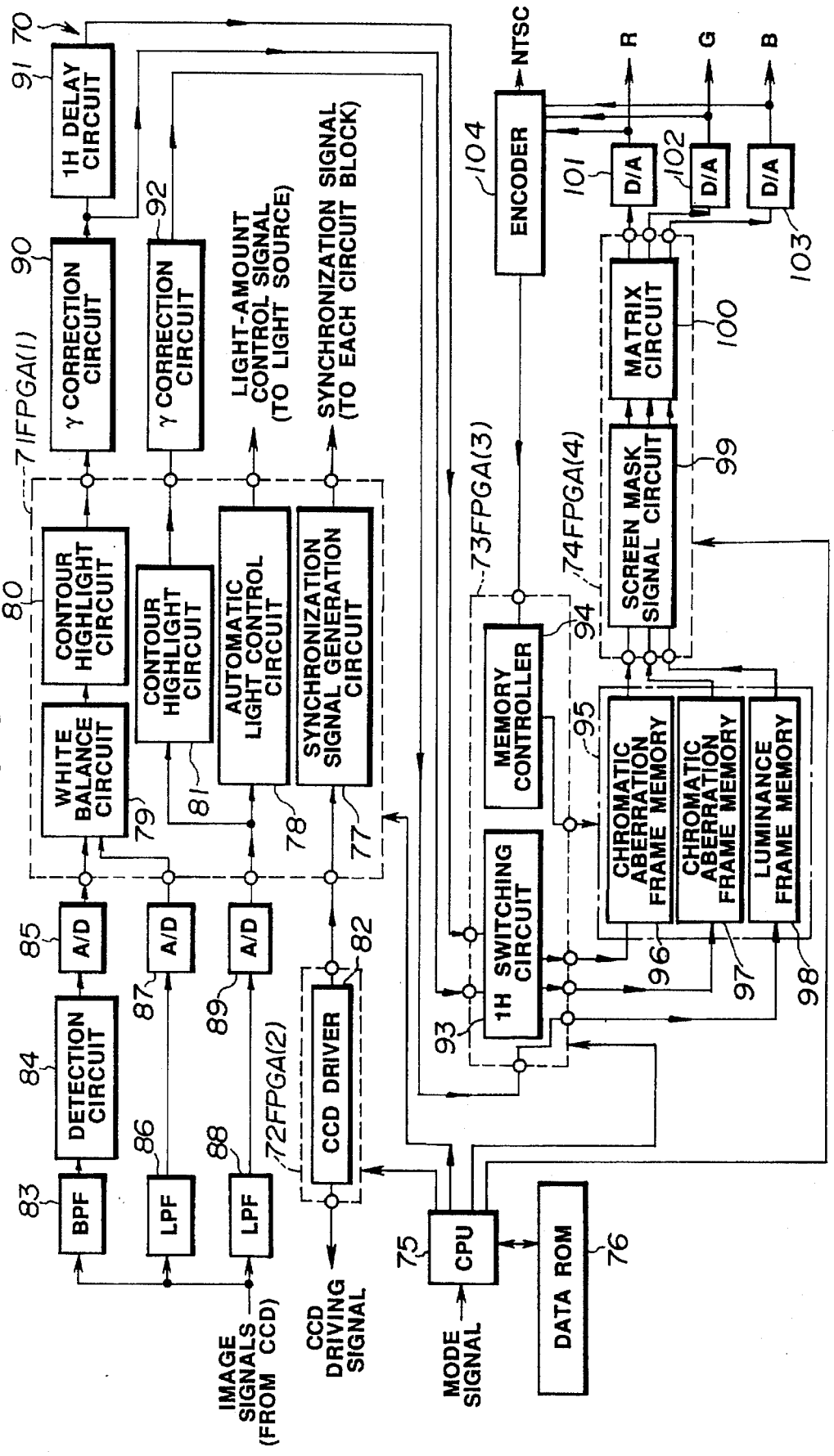
FIG. 8 is a block diagram illustrating a functional arrangement of a signal processing circuit in a case where a simultaneous system electroendoscope apparatus used for an NTSC system is connected to a camera control unit according to a fourth embodiment of the present invention.

FIG. 8 illustrates the arrangement of functions when a simultaneous system electroendoscope for use with NTSC TV signals is connected to the camera control unit 70. Four field programmable gate arrays ((FPGAs (1) to (4)) 71 to 74 are provided in the camera control unit 70. Each FPGA (1) to (4) is programmable on the basis of circuit data corresponding to the system of the electroendoscope. Namely, the arrangement of circuit functions changes depending upon the imaging system of an electroendoscope connected and upon the TV system in conformity with output signals.

Each circuit of the FPGAs 71 to 74 is formed based on the circuit data output from the CPU 75. A data ROM 76 in which a plurality of circuit data is stored is connected to the CPU 75. The inputting of a mode signal for identifying the system of the endoscope to the CPU 75 from an electroendoscope or the like causes circuit data corresponding to the mode signal to be read out and written in the FPGAs 71 to 74. The mode signal is supplied by the electroendoscope or the like. The mode signal is only required to identify the type (the number of pixels) of CCDs provided in the endoscope, the imaging system, the TV system or the like.

When the simultaneous system electroendoscope for NTSC is connected to the camera control unit 70, the circuit of each of the FPGAs 71 to 74 is formed as shown in FIG. 8. The FPGA (1) 71 comprises a synchronization signal generation circuit 77, an automatic light-control circuit 78, a white balance circuit 79, and outline highlighting circuits 80 and 81. The FPGA (2) 72 comprises a CCD driver 82 for driving simultaneous system CCDs. The synchronization signal generation circuit 77 is designed to generate a synchronization signal required for each circuit. A synchronization signal generated by the synchronization signal generation circuit 77 is also supplied to the CCD driver 82 which drives simultaneous system CCDs (not shown) provided in an extreme end portion of the electroendoscope on the basis of the synchronization signal.

Figure 9:
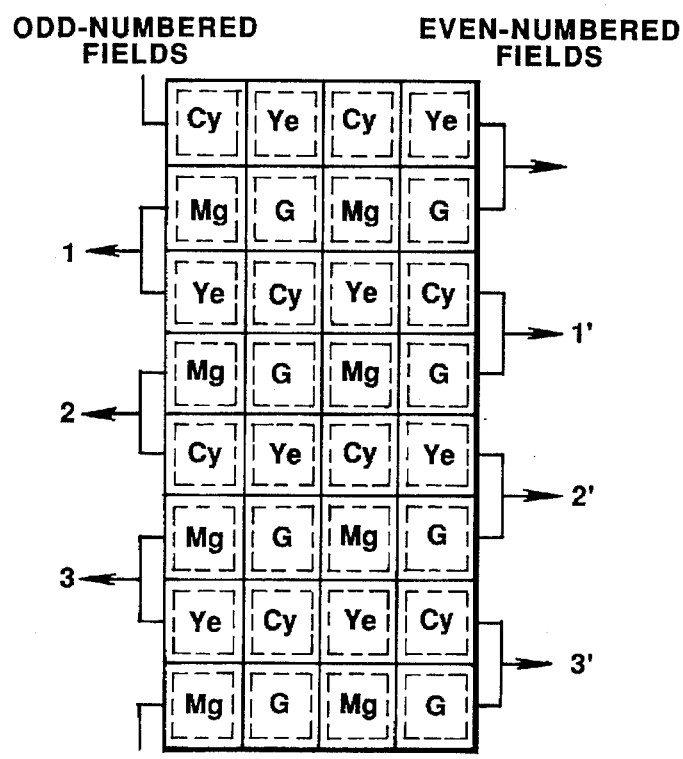
FIG. 9 is an illustration of a mosaic filter of a color difference sequential system according to the fourth embodiment.
Figure 10:
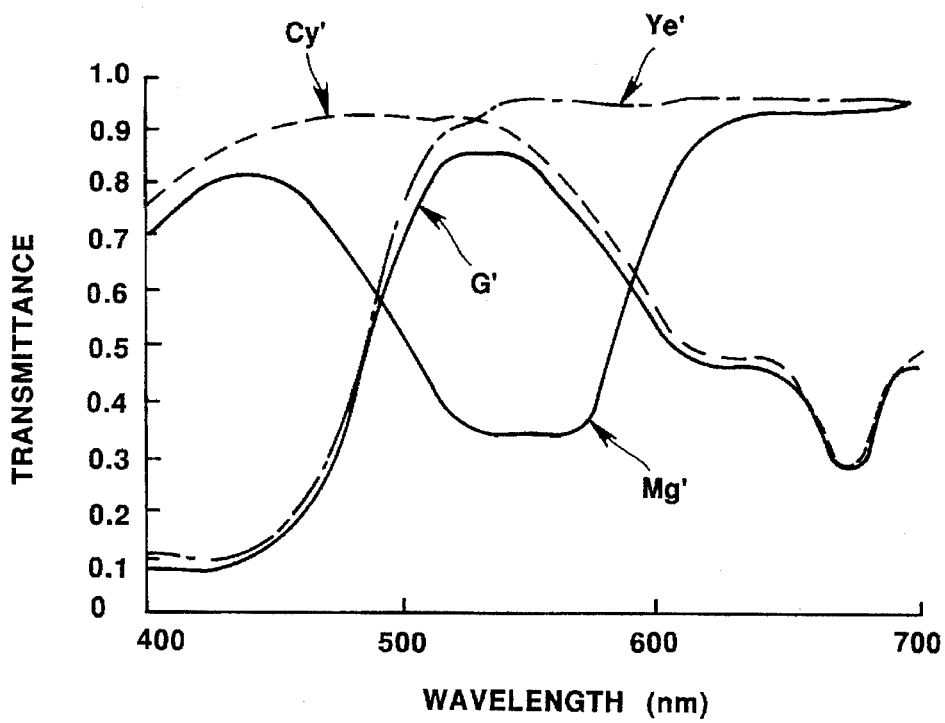
FIG. 10 is a characteristic view illustrating spectral characteristics of each filter of the mosaic filter of FIG. 9 according to the fourth embodiment.

A commonly used mosaic filter or the like of a color difference sequential system is provided in the imaging plane of the CCD of the simultaneous system electroendoscope of this embodiment. The structure of this mosaic filter is shown in FIG. 9. The mosaic filter comprises filters of four colors: Cy, Mg, Ye and G. The spectral characteristics of the filter of each color are shown in FIG. 10. The principles of color separation of such color difference sequential system are shown in FIGS. 11(a)–11(g).

Signal processing in the color difference sequential system will be explained with reference to FIGS. 11(a)–11(g) and 8.

Figure 11A:
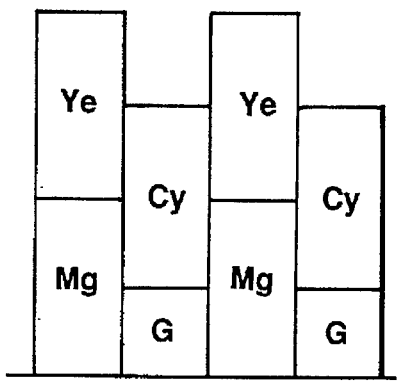
FIGS. 11(a)–11(g) illustrate the principles of color separation of the color difference sequential system according to the fourth embodiment.
Figure 11C:
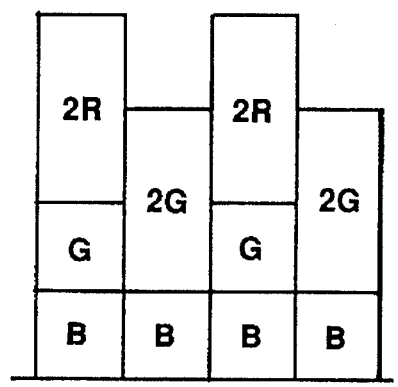
Figure 11B:
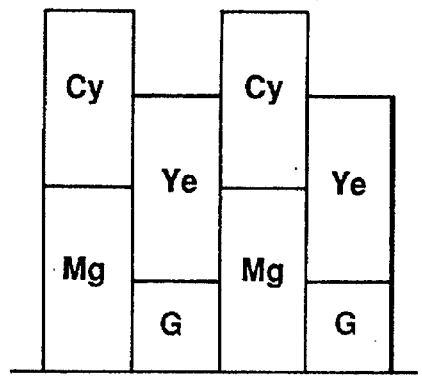
Figure 11D:
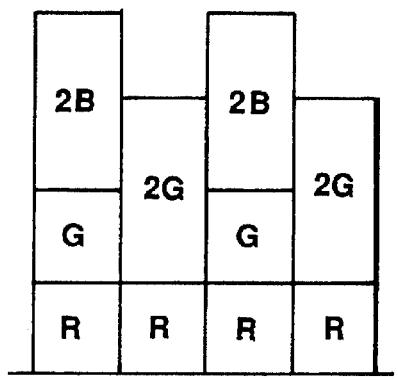

In this system, pixels of two rows are added and read out one after another in the mosaic filter shown in FIG. 9. At this time, rows of pixels, which are in odd-numbered fields, are shifted from those in even-numbered fields and read out. As a result, signals from odd-numbered scanning lines and those from even-numbered scanning lines are as shown in FIGS. 11(a) and 11(b), respectively. Color components of these signals from odd and even-numbered scanning lines are shown in FIGS. 11(c) and 11(d), respectively.

Figure 11E:
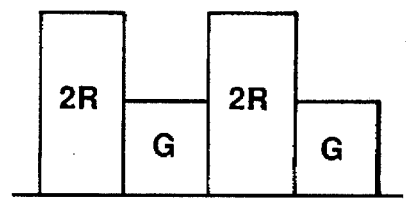
Figure 11G:
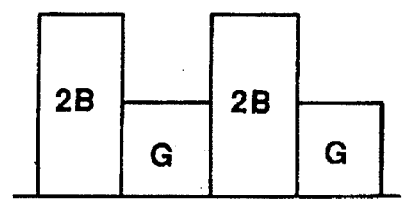
Figure 11F:
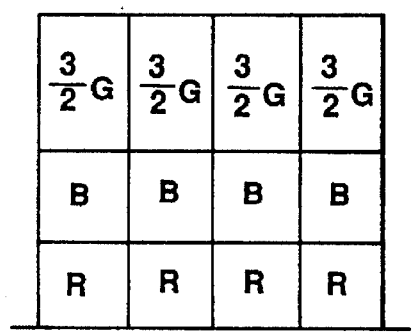

These image signals are input to a band pass filter (BPF) 83 and low-pass filters (LPF) 86 and 88. Color signal components having a central wavelength of 3.58 MHz are selected by the band pass filter 83 and a detection circuit 84, and color signal components of 2R−G and 2B−G are extracted as shown in FIGS. 11(e) and 11(g). Color signal components of (3/2) G+B+R shown in FIG. 11(f) are extracted by the low-pass filter 86.

Extracted color signals are converted into digital signals by A/D converters 85 and 87, and input to the white balance circuit 79, provided within the FPGA (1) 71, in which circuit the color signals are balanced. The signals are then outline-highlighted by the outline highlighting circuits 80 and input to a γ correction circuit 90 which is formed by ROM tables. After γ correction is performed by the γ correction circuit 90, the signals are delayed by 1 H by a 1H delay circuit 91.

At this time, a 1H switching circuit 93 and a memory controller 94 are formed in the FPGA (3) 73. By the 1H switching circuit 93 switching between the signals which are γ-corrected by the γ correction circuit 90 and the signals which are 1H delayed by the 1H delay circuit 91, color difference signals of 2R−G and 2B−G are obtained.

Furthermore, the brightness components of the image signals are separated by the low-pass filter 88 having a pass band of 3 MHz, and brightness signals of 2R+3G+2B are extracted. The obtained brightness signals are converted into digital data by an A/D converter 89 and input to the automatic light-control circuit 78 provided within the FPGA (1) 71. The automatic light-control circuit 78 generates a light-amount control signal for controlling the illumination light amount of the light source on the basis of the brightness signal level to be input and sends out this light-amount control signal to the light-source apparatus. The brightness signals input to the FPGA (1) 71 are outline-highlighted by the outline highlighting circuit 81 and thereafter γ-corrected by the γ correction circuit 92.

In this embodiment, an image memory 95 is composed of a frame memory group of color difference frame memories 96 and 97 and a brightness frame memory 98 for storing color difference signals and brightness signals. The color difference signals outputted from the 1H switching circuit 93 are recorded in the color difference frame memories 96 and 97. The brightness signals outputted from the γ correction circuit 92 are recorded in the brightness frame memory 98 after passing through the FPGA (3) 73 without change. Writing and reading control corresponding to the simultaneous system is performed in the image memory 95 by the memory controller 94 provided in the FPGA (3) 73. The reading of the image memory 95 is controlled by the memory controller 94 so as to conform to the frequency of the NTSC system.

FPGA (4) 74 is formed of a screen mask signal circuit 99 and a matrix circuit 100. Brightness signals and color difference signals recorded in the frame memories 96, 97 and brightness frame memory 98 are subjected to display area mask processing which is performed by the screen mask signal circuit 99 provided in the FPGA (4) 74. Then, the signals are converted from the brightness and color-difference signals into RGB video signals by the matrix circuit 100.

The converted RGB video signals are converted into analog video signals by D/A converters 101, 102 and 103 and displayed on a TV monitor or the like. The RGB video signals converted into analog video signals are also supplied to an encoder 104. The encoder 104 converts the RGB video signals into NTSC signals on the basis of a selection signal from the memory controller 94 and output them to a TV monitor or the like.

Figure 12:
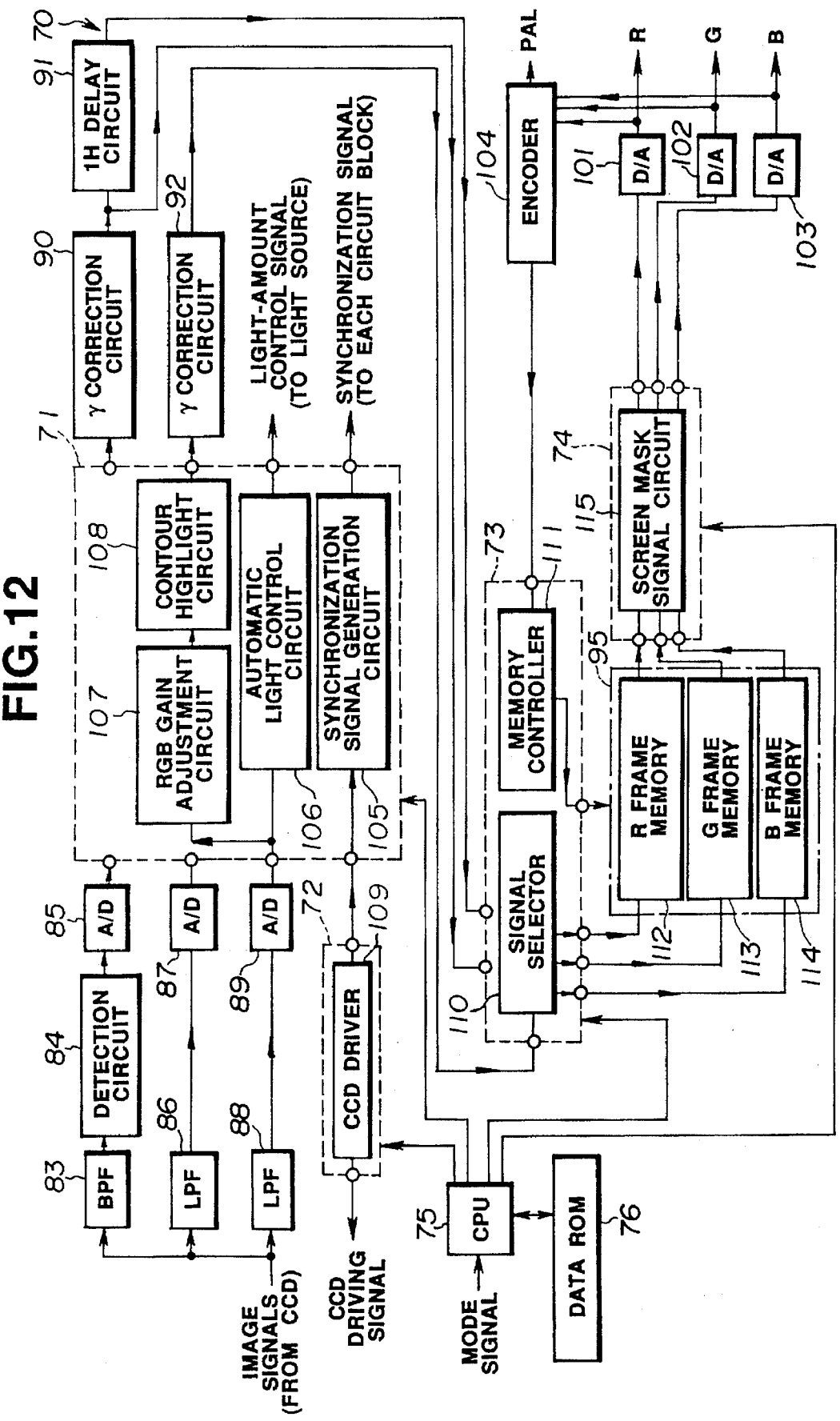
FIG. 12 is a block diagram illustrating a functional arrangement of a signal processing circuit when a surface sequential system electroendoscope apparatus used for a phase alteration by line (PAL) system is connected to the camera control unit according to the fourth embodiment.

Next, an example in which a surface sequential system electroendoscope for PAL is connected to the camera control unit 70 will be explained with reference to FIG. 12. FIG. 12 illustrates the arrangement of the functions of the camera control unit 70 when the surface sequential system electroendoscope for PAL is connected to the camera control unit 70.

The CPU 75 identifies the type of endoscope, the TV system or the like on the basis of a mode signal output from the connected electroendoscope and changes the circuit data of FPGAs 71 to 74. When the surface sequential system electroendoscope for PAL is connected to the camera control unit 70, a synchronization signal generation circuit 105, an automatic light-control circuit 106, a RGB gain adjustment circuit 107 and an outline highlighting circuit 108 are formed in the FPGA (1) 71. Also, a CCD driver 109 for driving surface sequential system CCDs is formed in the FPGA (2) 72.

The synchronization signal generation circuit 105 generates a synchronization signal required for each circuit in the same manner as does the synchronization signal generation circuit 77 in FIG. 8. This signal is then supplied to the CCD driver 109 which drives surface sequential system CCDs (not shown) provided in the extreme end portion of the electroendoscope.

Since RGB image data is obtained by CCDs in a time series manner in the surface sequential system, the bands of the image data read out from CCDs are limited by the low-pass filter 88. The image data is converted into digital data by the A/D converter 89 and input to the FPGA (1) 71. Signal lines from the A/D converters 85 and 87 are connected to the FPGA (1) 71 on the board, but are not connected within the FPGA (1) 71.

The automatic light-control circuit 106 generates a light-amount control signal for adjusting the illumination light amount of the light source on the basis of the signal level of an input digital image signal and sends out the light-amount control signal to the light source apparatus in the same manner as does the synchronization signal generation circuit 77 in FIG. 8.

The digital image signal from the A/D converter 89 is input to the RGB gain adjustment circuit 107 where white balance and color tone are adjusted by adjusting the gain of the RGB image signal inputted in a time series manner. After the level of each RGB image signal is adjusted by the RGB gain adjustment circuit 107, the outline of each RGB image signal is highlighted by the outline highlighting circuit 108.

At this time, a signal selector 110 and a memory controller 111 are formed in the FPGA (3) 73. The RGB image signal on which outline highlighting is performed by the outline highlighting circuit 108 is γ corrected by the γ correction circuit 92 and thereafter input to the signal selector 110. In the case of FIG. 12, the image memory 95 is formed of a frame memory group consisting of a R frame memory 112, a G frame memory 113, and a B frame memory 114, for storing RGB image signals. The signal selector 110 inputs RGB image signals inputted in a time series manner to frame memories 112, 113, and 114 for each of R, G and B of the image memory 95. Although the γ correction circuit 90 and the 1H delay circuit 91 are connected to FPGAs 71 and 73, respectively, on the board in this example, they are not connected within each FPGA.

A circuit is set in the memory controller 111 on the basis of circuit data from the CPU 75 corresponding to the mode signal. The memory controller 111 controls the writing of RGB image signals in the image memory 95, which signals are based on the surface sequential system and input in a time series manner. Namely, RGB image signals input in a time series manner are made into simultaneous signals in the image memory 95.

A screen mask signal circuit 115 is formed in the FPGA (4) 74. Screen mask processing dedicated for surface sequential system CCDs is performed on the RGB image signals which are made simultaneous by the screen mask signal circuit 115 provided within the FPGA (4) 74. Thereafter, the RGB image signals are converted into analog video signals by D/A converters 101, 102 and 103, and output to a TV monitor or the like. The RGB image signals converted into analog video signals are also supplied to the encoder 104 which converts the RGB image signals into TV signals of the PAL system on the basis of a selection signal from the memory controller 111 and which outputs them to a TV monitor or the like.

Even the case in which each signal processing system is changed depending upon differences in the number of pixels of the CCDs provided in the connected electroendoscope can be handled by the CPU 75 which reads the corresponding circuit data written in the data ROM 76 and changes the circuity of the FPGA on the basis of the circuit data.

As the camera control unit is formed of a FPGA whose circuitry can be changed as described above, a plurality of systems can be handled with a small amount of circuitry irrespective of differences in the imaging systems of the electroendoscope between the surface sequential system and the simultaneous system, differences in the TV system, for example, between the PAL system or NTSC system, or in differences in the number of pixels of CCDs.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included with the spirit and scope of the claims. The following claims are to be accorded the broadest interpretation, so as to encompass all such modifications and equivalent structures and functions.

What is claimed is:

1. An electroendoscope apparatus which uses a plurality of types of electroendoscopes having solid-state imaging devices of different specifications and which performs signal processing in conformity with a plurality of signal processing systems, comprising:

video memory means supplied with an output signal from any of said solid-state imaging devices, said video memory means being used commonly for said plurality of types of electroendoscopes and for said plurality of signal processing systems;

signal processing means connected to said video memory means said signal processing means having a memory control function for writing in and reading from said video memory means, and a signal processing function for processing signals written in and read from said video memory means, said signal processing means comprising a plurality of programmable logic elements consisting of a field programmable gate array;

means for recording circuit formation data for rearranging the formation of said programmable logic elements, said circuit formation data corresponding to at least one of said plurality of types of electroendoscopes and said plurality of signal processing systems being recorded in said means, and said circuit formation data being used for rearranging said programmable logic elements so as to render operative said memory control function and said signal processing function; and control means for rearranging the formation of said programmable logic elements in said signal processing means based on said circuit formation data, said control means being used for rearranging the formation of said programmable logic elements based on said circuit formation data corresponding to the type of the electroendoscope connected to said electroendoscope apparatus and the signal processing system, thereby to form a signal processing circuit exclusively used for said signal processing means, wherein said field programmable gate array in said signal processing means is adaptable for processing signals of solid state imaging devices which vary in a plurality of different specification parameters, including number of pixels, wherein said field programmable gate array in said signal processing means is adaptable for processing signals of both a surface sequential imaging system and a simultaneous imaging system, and wherein said field programmable gate array in said signal processing means is adaptable for processing signals of both a PAL TV system and an NTSC TV system.

2. An electroendoscope apparatus according to claim 1, further comprising:

a plurality of types of electroendoscopes having solid-state imaging devices of different specifications; and a video signal processing apparatus, having the plurality of types of electroendoscopes connected thereto, which apparatus performs signal processing in conformity with a plurality of signal processing systems.

3. An electroendoscope apparatus according to claim 2, wherein the circuit formation data recording means, provided in each of the plurality of types of electroendoscopes, records circuit formation data of the signal processing system corresponding to each of the electroendoscopes, and wherein the signal processing means forms a dedicated processing circuit corresponding to each of the electroendoscopes when circuit formation data corresponding to each of the electroendoscopes is input.

4. An electroendoscope apparatus according to claim 2, further comprising:

endoscope type identifying means for identifying the type of a connected electroendoscope, wherein the circuit formation data recording means, provided in each of the plurality of types of electroendoscopes, records circuit formation data of the signal processing system corresponding to each of the electroendoscopes, and wherein the signal processing means forms a dedicated processing circuit corresponding to each of the electroendoscopes when circuit formation data corresponding to each of the electroendoscopes in input.

5. An electroendoscope apparatus according to claim 3, wherein the circuit formation data recording means is formed of a recording medium, releasably mounted on the video signal processing apparatus or the electroendoscope, in which circuit formation data of a signal processing system corresponding to each of the plurality of types of electroendoscopes is recorded, and wherein the signal processing means forms a dedicated processing circuit corresponding to the signal processing system of the connected electroendoscopes when circuit formation data recorded in the circuit formation data recording means and corresponding to each electroendoscope is input.

6. An electroendoscope apparatus according to claim 1, wherein the signal processing means forms an imaging element driving circuit corresponding to each of the plurality of signal processing systems on the basis of the circuit formation data recorded in the circuit formation data recording means.

7. An electroendoscope apparatus according to claim 1, wherein the signal processing means forms a video signal processing circuit corresponding to each of the plurality of signal processing systems on the basis of the circuit formation data recorded in the circuit formation data recording means.

8. An electroendoscope apparatus according to claim 1 wherein at least one of the plurality of logic elements forms an imaging device driving circuit corresponding to each of the plurality of signal processing systems.

9. An electroendoscope apparatus according to claim 1, wherein the signal processing means forms an imaging element driving circuit and a video signal processing circuit which are capable of operating solid-state imaging devices having different number of pixels.

10. An electroendoscope apparatus according to claim 1, wherein the signal processing means forms an imaging element driving circuit and a video signal processing circuit conforming to a plurality of TV systems.

11. An electroendoscope apparatus according to claim 1, wherein the signal processing means forms an imaging element driving circuit and a video signal processing circuit conforming to a plurality of imaging systems.

* * * * *